(12) United States Patent
Dillenburg et al.

(10) Patent No.: US 6,416,555 B1
(45) Date of Patent: Jul. 9, 2002

(54) PROSTHESIS ATTACHMENT SYSTEM

(76) Inventors: Richard A. Dillenburg, 3802 S. Pleasant Pl., Chandler, AZ (US) 85248; David C. LaConte, 661 S. Ithica St., Chandler, AZ (US) 85225

(*) Notice: Subject to any disclaimer, the term of this patent is extended or adjusted under 35 U.S.C. 154(b) by 20 days.

(21) Appl. No.: 09/580,885

(22) Filed: May 30, 2000

(51) Int. Cl.[7] .................................................. A61F 2/54
(52) U.S. Cl. ........................................................ 623/65
(58) Field of Search .............................. 623/58, 59, 60, 623/61, 62, 65

(56) References Cited

U.S. PATENT DOCUMENTS

| | | | |
|---|---|---|---|
| 2,333,009 A | | 10/1943 | Hosmer |
| 2,561,523 A | * | 7/1951 | Lux ............................ 623/65 |
| 3,747,128 A | | 7/1973 | De Filipo |
| 3,802,302 A | * | 4/1974 | Bengtson ..................... 623/65 |
| 3,965,491 A | | 6/1976 | Frenzel |
| 4,357,717 A | | 11/1982 | Puhl |
| 4,661,113 A | | 4/1987 | Adkins |
| 4,944,765 A | | 7/1990 | Keith |
| 5,314,500 A | * | 5/1994 | Weddendorf ................. 623/65 |
| 5,464,444 A | | 11/1995 | Farquharson et al. |
| 5,800,572 A | | 9/1998 | Loveall |

FOREIGN PATENT DOCUMENTS

FR 484160 * 9/1917 ................. 623/65

* cited by examiner

Primary Examiner—Bruce Snow
(74) Attorney, Agent, or Firm—Schmeiser, Olsen & Watts

(57) ABSTRACT

An attachment for use with a prosthesis includes an adapter portion that is adapted to be secured to a prosthesis, a holder portion that is adapted to hold a handle, a connector portion that is pivotally attached to the adapter portion and that connects the adapter portion to the holder portion, and a stabilizing member connected to the adapter portion that is adapted to couple with a stabilizing wire lead extending from the prosthesis.

16 Claims, 3 Drawing Sheets

PROSTHESIS ATTACHMENT SYSTEM

BACKGROUND OF THE INVENTION

1. Technical Field

This invention relates to the field of prosthetic attachments. More specifically, the invention relates to new and useful improvements in an implement-holding attachment.

2. Background Art

Assorted prosthetic attachment devices have previously been provided. For instance, U.S. Pat. Nos. 3,747,128, 3,965,491, 4,357,717, and 4,661,113 employ handle-holding attachments for use in handling and swinging a golf club or other sporting implements.

However, these respective attachments have certain drawbacks. Specifically, U.S. Pat. No. 4,661,113 does not allow total universal pivotal movement during a swing due to a cross pin that extends through a ball portion of the pivoting joint. In addition, this device requires manipulation of the actual golf club itself to connect to the device. U.S. Pat. No. 4,357,717 allows for universal flexing or whipping motion during a swing, but does not allow any rotational motion. Furthermore, this device is non-conducive to grips on a golf club handle and has the potential to tear up the grip and underlying handle itself because of a set screw that secures the handle in place in the attachment. Moreover, none of the four heretofore mentioned devices are sufficiently stable during the swing.

SUMMARY OF THE INVENTION

What is needed is a prosthetic implement-holding attachment that overcomes the drawbacks of previous attachments. The invention solves these problems through an attachment for use with a prosthesis including an adapter portion that is adapted to be secured to a prosthesis, a holder portion that is adapted to hold a handle, a connector portion that pivotally connects the adapter portion to the holder portion, and a stabilizing member connected to the adapter portion that is adapted to couple with a stabilizing wire lead extending from the prosthesis.

A primary advantage of this invention is its allowance of total universal motion, yet stability during the swing in order to more readily control the golf club in its swing, reduce stress on the good wrist, and keep the prosthesis stable and securely attached to the handicapped arm during the swing. Therefore, the invention provides true wrist-like motion and a normal, controlled, stabilized swing.

Another advantage of the invention is its pivotal attachment between the adapter portion and the connector portion, which in the preferred embodiment is easily adjusted so as to be loose enough to move during the back swing, but tight enough to prevent excessive rotation during the swing.

Yet another advantage of the invention is its handle holding portion, which in the preferred embodiment is unitary and penannularly cylindrical, with the inner surface being tapered to more readily hold the golf club handle. The tapered inner surface also has a large surface area in contact with a golf club handle to reduce twist and slippage of the club. Golf club handles should not have to be manipulated to attach to the invention, and golf club handles and grips are not eaten up when used in conjunction with the invention.

The foregoing and other features and advantages of the invention will be apparent from the following more particular description of the preferred embodiment of the invention, as illustrated in the accompanying drawings.

BRIEF DESCRIPTION OF THE DRAWINGS

The preferred embodiment of the invention will hereinafter be described in conjunction with the appended drawings, where like designations denote like elements, and.

DETAILED DESCRIPTION OF THE PREFERRED EMBODIMENT

Figure 1:
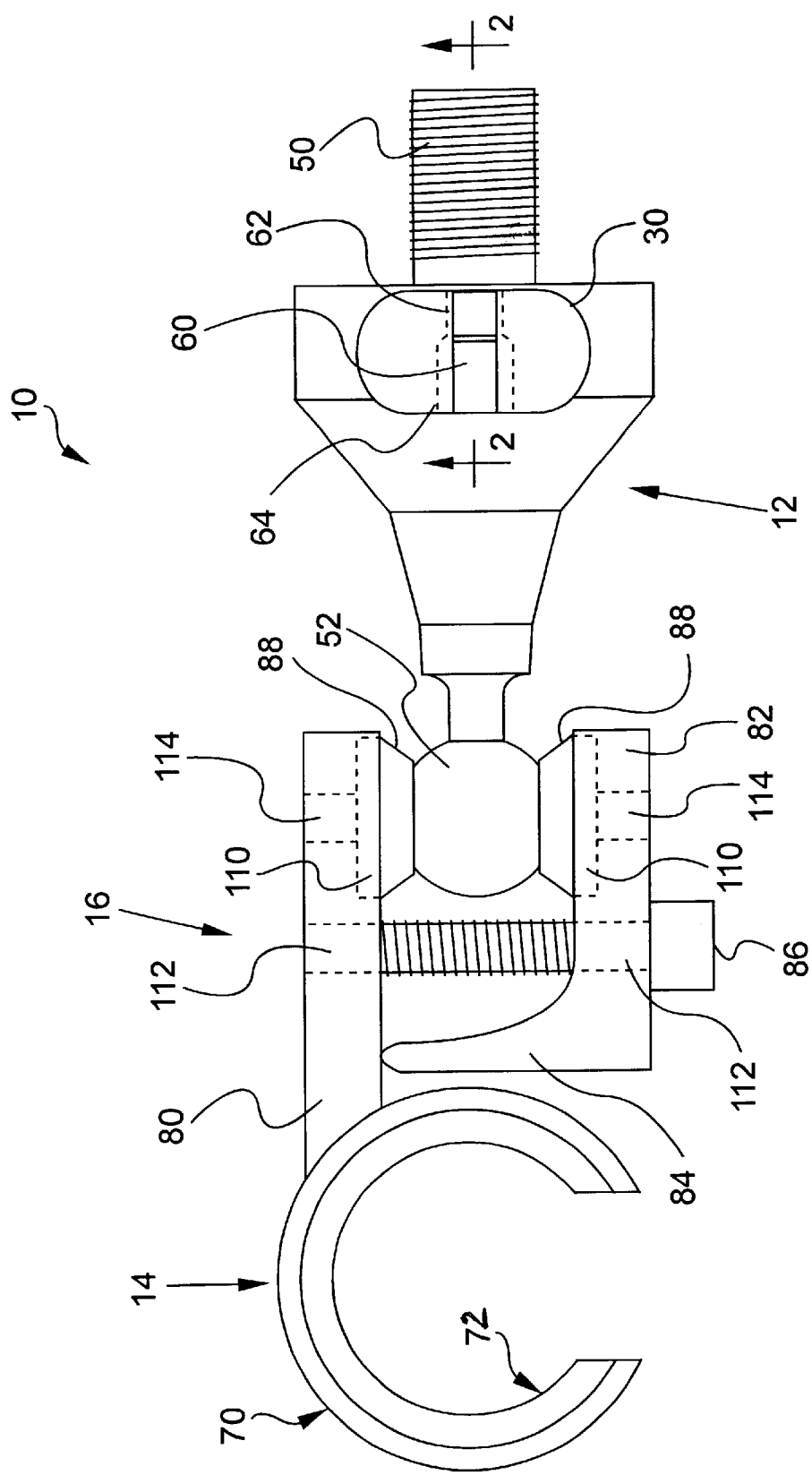
FIG. 1 is a top plan view of an embodiment of the invention.
Figure 2:
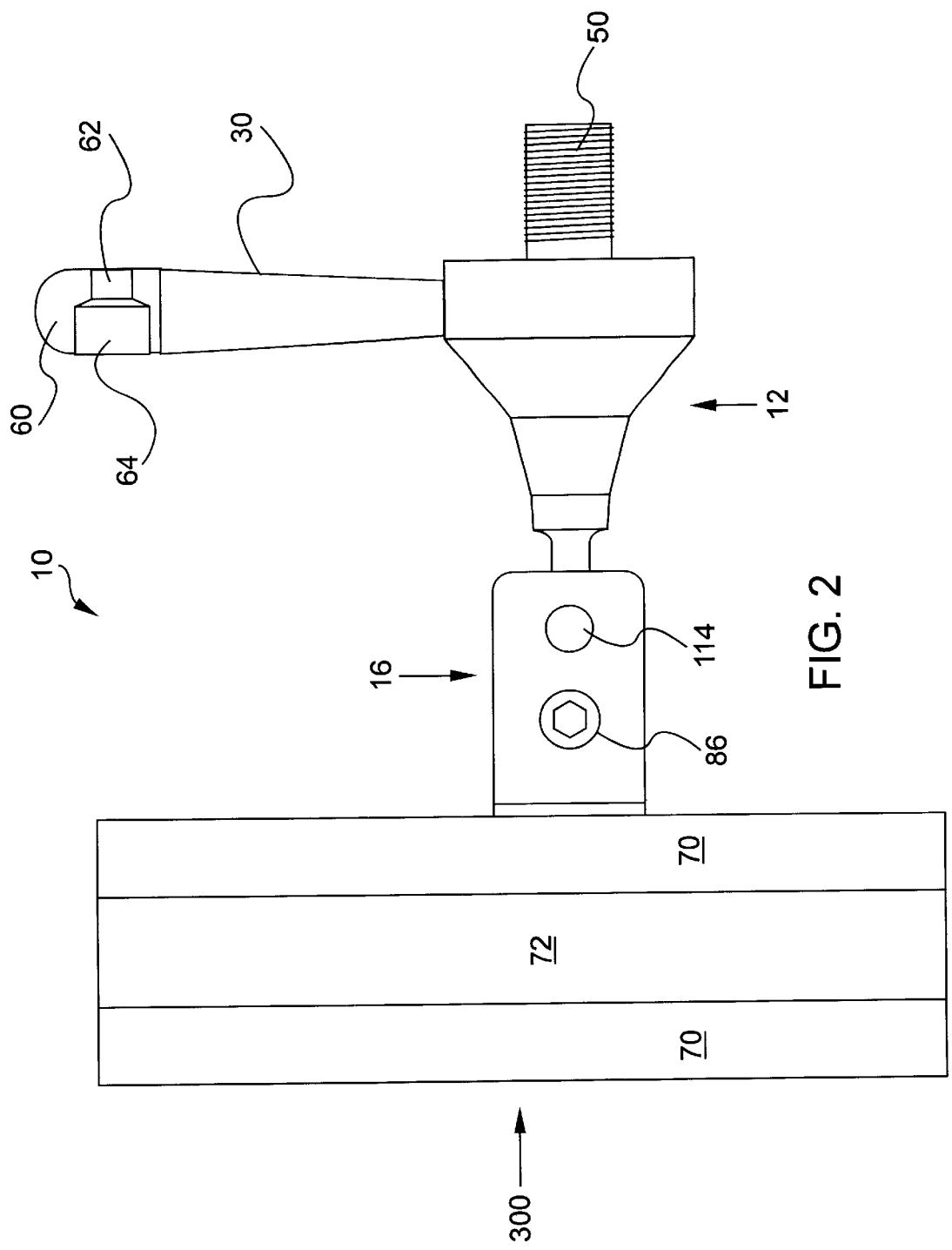
FIG. 2 is a front plan view of an embodiment of the invention with a partially broken away cross sectional view taken on the line 2—2 of FIG. 1.
Figure 3:
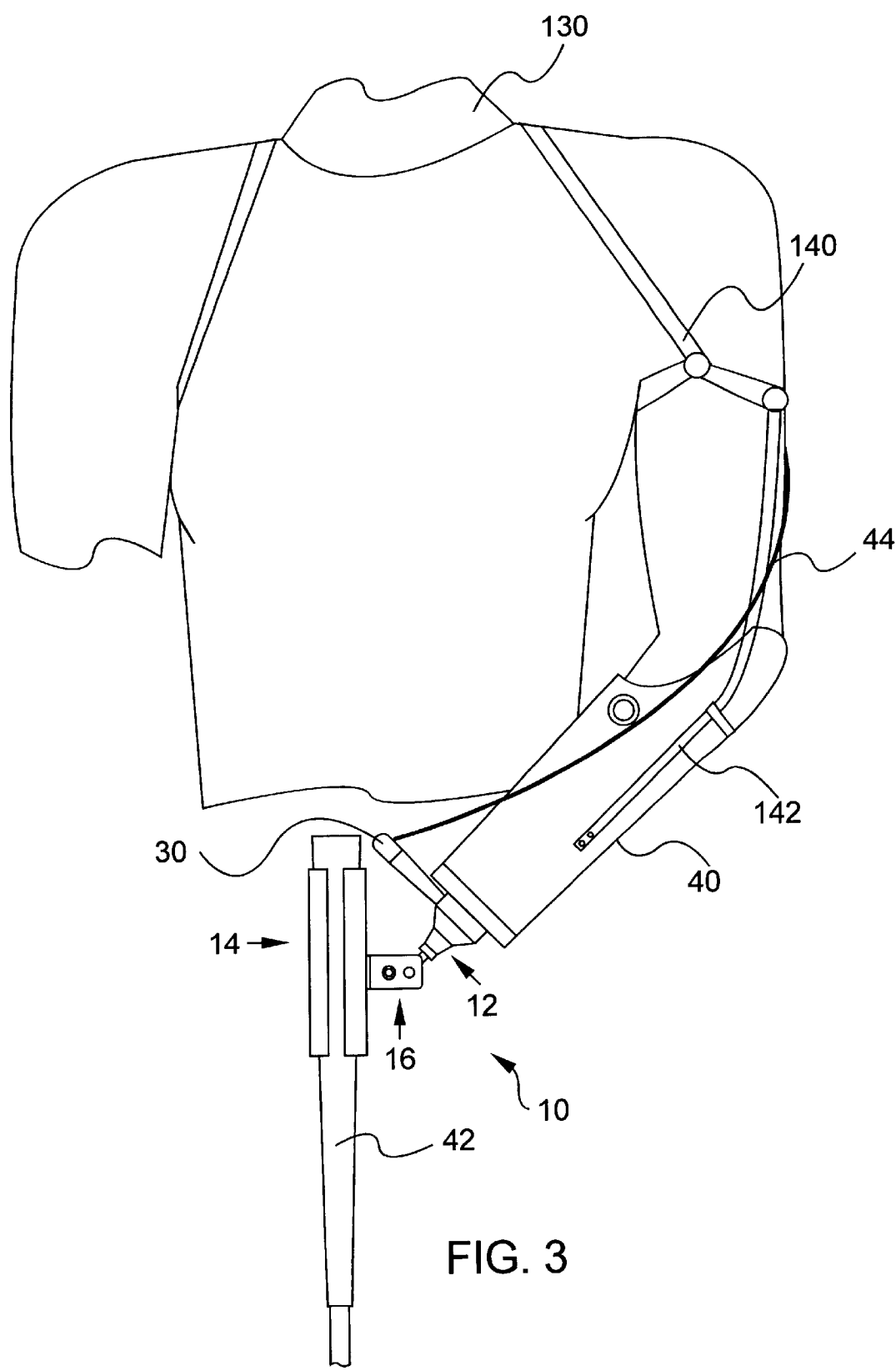
FIG. 3 is a partial perspective view of the invention being utilized by a golfer-amputee.

Referring to FIGS. 1–3, an attachment 10 generally includes an adapter portion 12, a holder portion 14, and a connector portion 16 that pivotally connects adapter portion 12 to holder portion 14. A stabilizing member 30 is connected to adapter portion 12. Adapter portion 12 is adapted to be secured to a prosthesis 40, while holder portion 14 is adapted to hold a handle 42. Stabilizing member 30 is adapted to couple with a stabilizing wire lead 44 extending from the prosthesis 40.

Attachment 10 allows total universal motion, yet stability, during the swing in order to more readily control the golf club in its swing, reduce stress on the good wrist, and keep the prosthesis 40 stable and securely attached to the handicapped arm during the swing. In addition, the pivotal attachment between adapter portion 12 and connector portion 16 is easily adjusted so as to be loose enough to move during the back swing, but tight enough to prevent excessive rotation during the forward swing. The tension in the pivotal attachment may be adjusted to provide varying degrees of tension in the pivotal attachment for different types of strokes with one simple adjustment. For example, the pivotal attachment may be tightened for driving, but loosened for chipping. Attachment 10 may hold virtually any golf club handle, as golf club handles do not have to be manipulated to attach to the invention. Moreover, golf club handles and grips are not eaten up when used in conjunction with holder portion 14.

Referring to FIGS. 1–2 and describing attachment 10 in greater detail, adapter portion 12 of attachment 10 includes a screw 50, a stabilizing member 30, and a ball 52. Screw 50 is located at a first end of adapter portion 12. Screw 50 removably engages with an end of prosthesis 40 that is not engaged with the handicapped arm. Although attachment 10 utilizes screw 50 of adapter portion 12 for removable engagement, it is also within the scope of the invention to secure the invention to any prosthesis by utilizing other adapting means, such as quick-release or snap-in devices. Furthermore, not all prostheses are the same due to the variations in handicapped arms. Therefore, the invention is easily capable through its manufacturing of being secured and adapted to other prostheses utilized in conjunction with handicapped arms.

Ball 52 is located at a second end of adapter portion 12 and forms a pivotal attachment with connector portion 16, to be described in more detail hereinafter. Although ball 52 is utilized by attachment 10 for creating a pivotal attachment between adapter portion 12 and holder portion 14, it is also within the concept of the invention that other components besides ball 52 might be used to create a pivotal attachment between the adapter portion 12 and holder portion 14, and that the pivotal attachment is not limited to ball and socket type joints.

Stabilizing member 30 is connected to and extends radially from adapter portion 12. Stabilizing member 30 defines an aperture 60 at an end of stabilizing member 30 distal from adapter portion 12. Aperture 60 is a penannularly channeled, cylindrical aperture including a first tier 62 and a second tier 64. Aperture 60 extends completely through stabilizing member 30 and a channel 66 extends radially outwardly from aperture 60. Channel 66 is capable of receiving a stabilizing wire lead 44. First tier 62 is adapted to either couple with or slidably receive the head of stabilizing wire lead 44, while the second tier 64 is adapted to stop the head from passing through aperture 60. Although stabilizing member 30 is preferred, the scope of the invention includes several other designs for a stabilizing member. For example, the scope of the invention includes a similar stabilizing member that defines an aperture, and a channel that extends from the aperture and through the stabilizing member, wherein the aperture is adapted to receive the head of a stabilizing wire lead and the channel is capable of letting the stabilizing wire lead pass through it.

Referring still to FIGS. 1–2, holder portion 14 of attachment 10 is preferably unitary and penannularly cylindrical and includes outer concentric surface 70 and tapered inner concentric surface 72. Although holder portion 14 is preferred, the holder portion of the invention may be adapted to hold different golf club handles. Furthermore, the holder portion of the invention may be only penannularly cylindrical, without the inner concentric surface being tapered, and the surfaces need not be concentric. Also, inner concentric surface 72 may be circumferentially ribbed. Holder portion 14 could include a hinge with a latching mechanism allowing other implements to be held.

Connector portion 16 of attachment 10 includes a first retaining member 80, a second retaining member 82, a third retaining member 84, a screw 86, and inserts 88. Retaining member 80 defines recess 110, aperture 112, and aperture 114. Retaining member 80 is attached to holder portion 14 at an end. Recess 110 is distal from retaining member 80 and receives insert 88, thereby forming a socket. Centrally located aperture 112 receives screw 86. Aperture 114 is preferably concentric with recess 110 and facilitates in the unseating of insert 88 of retaining member 80.

Retaining member 82 of connector portion 16 defines a recess 110, an aperture 112, and an aperture 114. Retaining member 82 is preferably not directly attached to holder portion 14. Instead, retaining member 82 is unitary with retaining member 84, wherein retaining members 82, 84 form an L-shape. Alternatively, retaining members 82, 84 could form any unitary shape variation sufficient to separate retaining member 82 from retaining member 80. Furthermore, retaining members 82, 84 do not have to be unitary, but rather they may be attached to each other in some other manner.

An end of retaining member 84 distal from retaining member 82 abuts retaining member 80. Retaining member 82 defines a recess 110 distal from retaining member 84 that opposes recess 110 in retaining member 80. Recess 110 receives insert 88, thereby forming a socket. Centrally located aperture 112 of retaining member 82 receives screw 86. Aperture 114 is preferably coaxial with recess 110 and facilitates in the unseating of insert 88 of retaining member 82. Screw 86 of connector portion 16 adjustably attaches retaining member 82 to retaining member 80 through removable threaded engagement by way of apertures 112 on respective retaining members 80 and 82, preferably without screw 86 touching ball 52.

Inserts 88 are seated in recesses 110 on respective retaining members 80 and 82, thereby forming sockets. Inserts 88 abut ball 52 of adapter portion 12 on opposite sides of ball 52. The attachment of retaining member 82 to retaining member 80 by adjustable screw 86 secures ball 52 of adapter portion 12 in place between the respective sockets created by inserts 88. As screw 86 is adjustably tightened, bringing retaining members 80 and 82 closer together, inserts 88 are compressed against ball 52. As screw 86 is adjustably loosened, inserts 88 are decompressed from ball 52. Thus, the combination of retaining member 80, retaining member 82, retaining member 84, screw 86, and inserts 88 in conjunction with ball 52 of adapter portion 12 form an adjustable pivotal attachment.

Although connector portion 16 preferably includes retaining member 80, retaining member 82, retaining member 84, recesses 110, apertures 112, apertures 114, screw 86, and inserts 88, the connector portion of the invention my be defined by various alternative components. For example, the connector portion could include two opposite retaining members, each connected to the holder portion of the invention at an end, and each including a socket at the other end capable of forming a pivotal attachment with ball 52 of the adapter portion of the invention. Furthermore, the connector portion could include three separate retaining members, wherein two retaining members are opposite each other, and each are connected to the holder portion of the invention at an end, and each include a socket at the other end capable of forming a pivotal attachment with ball 52 of the adapter portion of the invention. A third retaining member could extend between the two retaining members and the two retaining members each have an aperture capable of receiving a screw, thus allowing for an adjustable attachment between the two retaining members.

Holder portion 14 may include ribs that extend circumferentially about inner concentric surface 72. Such can be any width or height, and may aid in the holding of golf club handle 42 (FIG. 3), yet they should not be so protruded or sharp so as to damage or eat up golf club handle 42.

Attachment 10 may be made from any of many different types of materials. Preferably, attachment 10 is made from a metal, such as stainless steel or aluminum. Preferably, attachment 10 is made from 17-4 preheat treated stainless steel. Nevertheless, attachment 10 might be made from other materials, such as composites or polymers. Moreover, any of these suggested materials or other materials not mentioned may be combined together in any number of ways, and make-up any component, to create attachment 10. Inserts 88 of attachment 10 preferably are elastomeric inserts that are sufficiently stiff to stop excessive rotation, yet sufficiently resilient to allow a desired amount of rotation when screw 86 is adjusted to compress inserts 88 against ball 52. Preferably, the inserts 88 are made from the material sold under the name DELRON by Dupont.

Adapter portion 12, holder portion 14, and connector portion 16 of attachment 10 are manufactured separately and then assembled together. Manufacture of these components starts with either milling or casting the components defining attachment 10, with ensuing steps of attaching one end of retaining member 80 of connector portion 16 to holder portion 14, and attaching one end of stabilizing member 30 to adapter portion 12. These attachments might be welds. A possible subsequent step is sand blasting or polishing the components. Finally, inserts 88 are seated in recesses 110, ball 52 is placed between inserts 88, and retaining member 82 is attached to retaining member 80 by screw 86, thus forming the pivotal attachment between connector portion 16 and ball 52 of adapter portion 12.

For the use of attachment 10, reference is made to FIG. 3. In FIG. 3, attachment 10 is shown in conjunction with golfer-amputee 130. Adapter portion 12 is removably attached to prosthesis 40 and holder portion 14 is slidably engaged with golf club handle 42. Stabilizing member 30 is engaged with stabilizing wire lead 44. Prosthesis 40 is maintained on the handicapped arm of golfer-amputee 130 by harness 140 in conjunction with strap 142 and stabilizing wire lead 44.

Holder portion 14 easily slides into engagement with golf club handle 42 because holder portion 14 is penannularly cylindrical and inner concentric surface 72 is tapered. Because holder portion 14 is penannularly cylindrical with a penannular width slightly greater than a golf club shaft, it is able to slide on to virtually any golf club shaft at a point below golf club handle 42. Furthermore, inner concentric surface 72 has a taper that is preferably substantially opposite to the taper of golf club handle 42, allowing holder portion 14 to slidably engage and wedge itself against golf club handle 42, and thereby preventing golf club handle 42 from slipping, twisting, or being released accidentally during a swing or while holding the golf club in various positions. Thus, virtually any golf club may be securely held by holder portion 14, as golf club handles do not have to be manipulated to attach to the invention. Moreover, golf club handles and grips are not eaten up when engaged with the holder portion 14, but are nevertheless held securely by the wedged engagement.

The universal pivotal attachment between adapter portion 12 and connector portion 16 is easily adjustable by screw 86. As screw 86 is adjustably tightened, bringing retaining members 80 and 82 closer together, inserts 88 are compressed against ball 52. As screw 86 is adjustably loosened, inserts 88 are decompressed from ball 52. Thus, the universal pivotal attachment between adapter portion 12 and connector portion 16 may be adjusted so as to be loose enough to move during the back swing, but tight enough to prevent excessive rotation during the forward swing. One simple adjustment varies the stiffness of the pivotal attachment for different types of strokes.

Attachment 10 and its adjustable universal pivotal attachment between adapter portion 12 and connector portion 16 is utilized in conjunction with: stabilizing wire lead 44; prosthesis 40 of a well known type that engages the handicapped arm of golfer-amputee 130; harness 140 of a well known type that engages the neck and shoulders of golfer-amputee 130; and strap 142 of a well known type that is attached to prosthesis 40 and harness 140 and facilitates in holding prosthesis 40 to the handicapped arm. The use of these components in combination by golfer-amputee 130 while swinging a golf club allows the golf club to be readily controlled in its swing and reduce stress on the good wrist of golfer-amputee 130. In addition, when stabilizing wire lead 44 is coupled with stabilizing member 30, golfer-amputee 130 may flex the back muscles and tighten stabilizing wire lead 44 in order to provide additional stability during the swing. The engagement of stabilizing wire lead 44 to stabilizing member 30 also keeps prosthesis 40 stable and securely attached to the handicapped arm during a swing.

While the invention has been particularly shown and described with reference to a preferred embodiment thereof, it will be understood by those skilled in the art that various changes in form and details may be made therein without departing from the spirit and scope of the invention.

What is claimed is:

1. An apparatus for use with a prosthesis, the apparatus comprising:
   a) an adapter portion that is adapted to be secured to the prosthesis;
   b) a holder portion that is adapted to hold a handle;
   c) a connector portion pivotally connecting the adapter portion to the holder portion, wherein the connector portion comprises:
      1) a first retaining member connected to the holder portion at a first end, wherein the first retaining member comprises a socket that comprises a resilient insert that receives a portion of a ball of the adapter portion; and
      2) an opposite second retaining member, wherein the second retaining member comprises a socket that comprises a resilient insert that receives a portion of the ball of the adapter portion; and
   d) a stabilizing member connected to the adapter portion, wherein the stabilizing member is adapted to couple with a stabilizing lead extending from the prosthesis.

2. An apparatus for use with a prosthesis, the apparatus comprising:
   a) an adapter portion that is adapted to be secured to the prosthesis;
   b) a holder portion that is adapted to hold a handle;
   c) a connector portion pivotally connecting the adapter portion to the holder portion, wherein the connector portion comprises:
      1) a first retaining member connected to the holder portion at a first end, wherein the first retaining member comprises a socket that receives a portion of a ball of the adapter portion and wherein the first retaining member defines an aperture between the first end and the socket, the aperture being capable of receiving a screw;
      2) an opposite second retaining member connected to the holder portion at a first end, wherein the second retaining member comprises a socket that receives a portion of the ball of the adapter portion and wherein the second retaining member defines an aperture between the first end and the socket, the aperture being capable of receiving a screw;
      3) a third retaining member extending from the first end of the first retaining member to the first end of the second retaining member; and
      4) a screw that adjustably attaches the first retaining member and socket to the second retaining member and socket by way of the apertures, thereby forming an adjustable pivot with the ball of the adapter portion and the two sockets; and
   d) a stabilizing member connected to the adapter portion, wherein the stabilizing member is adapted to couple with a stabilizing lead extending from the prosthesis.

3. The apparatus of claim 2, wherein a first end of the third retaining member abuts the first end of the first retaining member and a second end of the third retaining member is fixed to the first end of the second retaining member.

4. The apparatus of claim 2, wherein the second retaining member and third retaining member are unitary, and wherein the unitary retaining member is attached to the first retaining member by the screw.

5. The apparatus of claim 2, wherein the screw does not touch the ball of the adapter portion.

6. An apparatus for use with a prosthesis, the apparatus comprising:
   a) an adapter portion with a ball at a first end and a screw at a second end;
   b) a unitary, penannularly cylindrical, holder portion defining an inner surface and an outer surface;
   c) a connector portion for connecting the adapter portion to the holder portion, the connector portion comprising a first end connected to the holder portion and a second end defining a socket that is pivotally joined with the ball of the adapter portion; and d) a stabilizing member connected to the adapter portion at a first end, wherein a second end of the stabilizing member defines an aperture and a channel that extends from the aperture and through the stabilizing member, wherein a stabilizing wire lead extending from the prosthesis may pass through the channel and wherein the aperture may receive a head of the stabilizing wire lead.

7. The apparatus of claim 6, wherein the inner surface holder portion is tapered.

8. The apparatus of claim 7, wherein the connector portion comprises:
   1) a first retaining member connected to the holder portion at a first end, wherein the first retaining member comprises a socket that receives a portion of the ball of the adapter portion and wherein the first retaining member defines an aperture between the first end and the socket, the aperture being adapted to receive a screw;
   2) an opposite second retaining member connected to the holder portion at a first end, wherein the second retaining member comprises a socket that receives a portion of the ball of the adapter portion and wherein the second retaining member defines an aperture between the first end and the socket, the aperture being adapted to receive the screw;
   3) a third retaining member extending from the first end of the first retaining member to the first end of the second retaining member; and
   4) a screw that adjustably attaches the first retaining member and socket to the second retaining member and socket by way of the apertures, thereby forming an adjustable pivot with the ball of the adapter portion and the two sockets.

9. The apparatus of claim 8, wherein a first end of the third retaining member abuts the first end of the first retaining member and a second end of the third retaining member is fixed to the first end of the second retaining member.

10. The apparatus of claim 8, wherein the second retaining member and third retaining member are unitary, and wherein the unitary retaining member is attached to the first retaining member by the screw.

11. The apparatus of claim 6, wherein the aperture of the stabilizing member is a channeled, two-tiered aperture extending completely through the stabilizing member, wherein a first tier of the aperture is adapted to couple with a head of the stabilizing wire lead and a smaller second tier is adapted to stop the head from sliding completely through the aperture.

12. The apparatus of claim 11, wherein the aperture of the second end of the stabilizing member is a channeled, two-tiered aperture extending completely through the stabilizing member, wherein a first tier of the aperture is adapted to slidably receive a head of the stabilizing wire lead and a smaller second tier is adapted to stop the head from sliding completely through the aperture.

13. An apparatus for use with a prosthesis, the apparatus comprising:
   a) an adapter portion with a ball at a first end and a screw at a second end;
   b) a unitary, penannularly cylindrical, holder portion defining an inner concentric surface and outer concentric surface, wherein the inner concentric surface is tapered;
   c) a connector portion for connecting the adapter portion to the holder portion, the connector portion comprising:
      1) a first retaining member connected to the holder portion at a first end, wherein the first retaining member comprises a socket that receives a portion of the ball of the adapter portion and wherein the first retaining member defines an aperture between the first end and the socket, the aperture being capable of receiving a screw;
      2) an opposite second retaining member connected to the holder portion at a first end, wherein the second retaining member comprises a socket that receives a portion of the ball of the adapter portion and wherein the second retaining member defines an aperture between the first end and the socket, the aperture being capable of receiving a screw;
      3) a third retaining member extending from the first end of the first retaining member to the first end of the second retaining member; and
      4) a screw that adjustably attaches the first retaining member and socket to the second retaining member and socket by way of the apertures, thereby forming an adjustable pivot with the ball of the adapter portion and the two sockets; and
   d) a stabilizing member connected to the adapter portion at a first end, wherein a second end of the stabilizing member defines a channeled, two-tiered aperture extending completely through the stabilizing member, wherein the channel is adapted to receive a stabilizing wire lead extending from the prosthesis, a first tier of the aperture is adapted to slidably receive a head of the stabilizing wire lead, and a smaller second tier is adapted to stop the head from sliding completely through the aperture.

14. The apparatus of claim 13, wherein the aperture of the stabilizing member connected to the adapter portion is a penannularly channeled, cylindrical, two-tiered aperture extending completely through the member.

15. The apparatus of claim 14, wherein the socket of the first retaining member and the socket of the second retaining member are identical, wherein the identical sockets comprise elastomeric inserts that fit into recesses in the respective retaining members.

16. The apparatus of claim 15, wherein the second retaining member and the third retaining member form a unitary retaining member that is attached to the first retaining member by the screw.

* * * * *